(12) United States Patent
Olson

(10) Patent No.: US 10,518,002 B2
(45) Date of Patent: Dec. 31, 2019

(54) INTRAOCULAR DRUG DELIVERY AND FILTER DEVICE AND METHODS OF USING SAME

(71) Applicant: The Regents of the University of Colorado, a body corporate, Denver, CO (US)

(72) Inventor: Jeffrey Olson, Denver, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 0 days.

(21) Appl. No.: 14/916,659

(22) PCT Filed: Sep. 8, 2014

(86) PCT No.: PCT/US2014/054531
§ 371 (c)(1),
(2) Date: Mar. 4, 2016

(87) PCT Pub. No.: WO2015/035296
PCT Pub. Date: Mar. 12, 2015

(65) Prior Publication Data
US 2016/0193391 A1    Jul. 7, 2016

Related U.S. Application Data

(60) Provisional application No. 61/874,759, filed on Sep. 6, 2013.

(51) Int. Cl.
| | |
|---|---|
| *A61K 41/00* | (2006.01) |
| *A61L 31/14* | (2006.01) |
| *A61L 31/16* | (2006.01) |
| *A61L 31/02* | (2006.01) |
| *A61K 9/00* | (2006.01) |
| *A61F 9/00* | (2006.01) |

(52) U.S. Cl.
CPC .......... *A61L 31/026* (2013.01); *A61F 9/0017* (2013.01); *A61K 9/0051* (2013.01); *A61K 41/0028* (2013.01); *A61L 31/028* (2013.01); *A61L 31/146* (2013.01); *A61L 31/16* (2013.01); *A61L 2300/112* (2013.01)

(58) Field of Classification Search
CPC .................................................. A61K 41/0028
See application file for complete search history.

(56) References Cited

U.S. PATENT DOCUMENTS

| | | | | |
|---|---|---|---|---|
| 2002/0026176 A1* | 2/2002 | Varner | ................... | A61F 9/0017 604/891.1 |
| 2005/0004663 A1* | 1/2005 | Llanos | .................... | A61L 31/16 623/1.46 |
| 2006/0110428 A1* | 5/2006 | deJuan | ................... | A61F 9/0017 424/427 |
| 2006/0235367 A1* | 10/2006 | Takashima | ........... | A61F 9/00781 604/541 |
| 2007/0150058 A1* | 6/2007 | Shahinpoor | ............... | A61F 2/08 623/14.13 |
| 2008/0147021 A1 | 6/2008 | Jani | | |
| 2008/0269318 A1* | 10/2008 | Romano | .............. | A61K 31/381 514/443 |
| 2010/0034864 A1 | 2/2010 | Spedden et al. | | |
| 2011/0098640 A1* | 4/2011 | Horne | .................. | A61K 9/0009 604/93.01 |
| 2011/0117169 A1 | 5/2011 | Sanford et al. | | |

FOREIGN PATENT DOCUMENTS

| | | |
|---|---|---|
| WO | 2006110487 | 10/2006 |
| WO | WO2012/149468 | * 4/2012 |
| WO | 2012149468 | 11/2012 |
| WO | 2013003620 | 1/2013 |

OTHER PUBLICATIONS

Katschke et al. Inhibiting Alternative Pathway Complement Activation by Targeting the Factor D Exosite. Jan. 2012.*
Gasche et al. Complement Depletion During Haemofiltration with Polyacrilonitrile membranes. 1996.*
Guilliams. Free Radicals, Antioxidants and Eye Diseases. Not as Incurable as We Once Thought. 1999.*
Stanton et al. Complement Factor D in Age-Related Macular Degeneration. Invest Opthalmol Vis Sci. Nov. 2011; 52(12):8828-8834.*
Jones. The Effect of Heat on Antibodies. Department of Animal Pathology of the Rockerfeller Insiute of Medical Research. 1927.*
Heier. Twin Lampalizumab Trials Fail to Impact Area of Geographic Atrophy. Nov. 2017.*
Harris et al. Development in Anti-Complement Therapy; From Disease to Clinical Trial. Molecular Immunology 102(2018) 88-119. Aug. 2018.*
Extended European Search Report dated May 15, 2017 in European Application No. 14842818.8.
Notification of International Search Report and the Written Opinion in International Application No. PCT/US2014/054531 dated Feb. 19, 2015.
Notification of International Preliminary Report on Patentability in International Application No. PCT/US2014/054531 dated Mar. 17, 2016.

* cited by examiner

*Primary Examiner* — David J Blanchard
*Assistant Examiner* — Sarah Alawadi
(74) *Attorney, Agent, or Firm* — Snell & Wilmer L.L.P.

(57) ABSTRACT

The present disclosure provides an implantable device comprising a substrate capable of capturing an intraocular target molecule and to methods of use thereof.

20 Claims, 5 Drawing Sheets

INTRAOCULAR DRUG DELIVERY AND FILTER DEVICE AND METHODS OF USING SAME

PRIORITY CLAIM

This application is a U.S. 371 National Stage Application of PCT Application No. PCT/US14/54531, filed Sep. 8, 2014, which claims priority to U.S. provisional patent application Ser. No. 61/874,759, filed on Sep. 6, 2013, the entire contents of which are incorporated herein by reference in their entirety.

BACKGROUND

Many ocular disorders are caused by or associated with one or more proteins; some such proteins are vasoactive compounds like vascular endothelial growth factor (VEGF), complement factors, and inflammatory factors. Current treatments typically attempt to decrease levels and effects of VEGF. Studies have shown that existing treatments are costly and rely on repeat injections. Further, endogenous proteins may be associated with progressive retinal degeneration, such as non-exudative macular degeneration. A need exists for improved treatments for ocular disorders, and particularly long-term treatment regimens that do not require repeat intraocular injections.

SUMMARY

In various embodiments, the present disclosure provides an implantable device comprising a substrate capable of capturing a target molecule present intraocularly (e.g., an intraocular target molecule). In some embodiments, the device is capable of being regenerated in situ.

In various embodiments, the present disclosure provides an implantable device comprising a substrate comprising one or more of hydroxyapatite and a ceramic (e.g., a bioceramic), and a captured angiogenic compound.

In various embodiments, the present disclosure provides a method of treating an ocular disorder in a subject, the method comprising implanting into an eye of the subject a device comprising a substrate capable of capturing a target molecule present in the eye or in fluid of the eye (e.g., an intraocular target molecule); and capturing the target molecule from the eye or from fluid of the eye. In some embodiments, the device is implanted into the eye such that the device extends into the vitreous cavity and/or the anterior chamber of the eye. In some embodiments, the method further comprises, after capturing the target molecule from the eye or from fluid of the eye, regenerating the device in situ. In some embodiments, the method further comprises, after the step of regenerating the device in situ, capturing the target molecule from the eye and/or from fluid of the eye. In another embodiment, fluid from the eye may be shunted outside the eye. For example and without limitation, fluid may be shunted from the eye using a glaucoma shunting device or similar apparatus. In one embodiment, a filtering device as described herein may be placed in the reservoir of the shunting device to remove angiogenic proteins from the fluid before the fluid is returned to the eye.

These and other embodiments of the present invention will be disclosed in further detail herein below.

DETAILED DESCRIPTION

Figure 1:
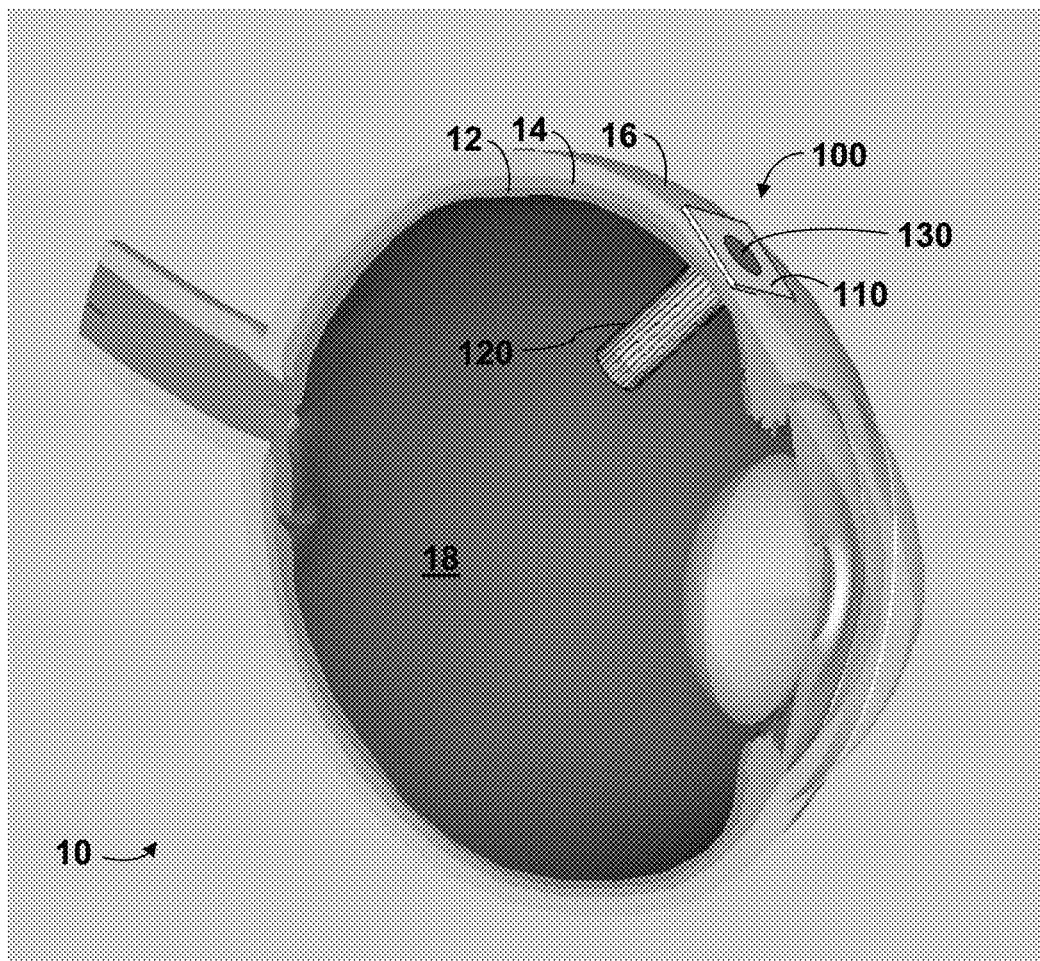
FIG. 1 depicts a device of the present disclosure implanted in an eye of a subject.

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." Also, the disclosure of ranges is intended as a continuous range including every value between the minimum and maximum values recited as well as any ranges that can be formed by such values. Also disclosed herein are any and all ratios (and ranges of any such ratios) that can be formed by dividing a disclosed numeric value into any other disclosed numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present invention.

The term "treatment" in relation a given disease or disorder, includes, but is not limited to, inhibiting the disease or disorder, for example, arresting the development of the disease or disorder; relieving the disease or disorder, for example, causing regression of the disease or disorder; or relieving a condition caused by or resulting from the disease or disorder, for example, relieving, preventing or treating symptoms of the disease or disorder. The term "prevention" in relation to a given disease or disorder means: preventing the onset of disease development if none had occurred, preventing the disease or disorder from occurring in a subject that may be predisposed to the disorder or disease but has not yet been diagnosed as having the disorder or disease, and/or preventing further disease/disorder development if already present.

In one embodiment, the present disclosure provides a method of treatment of an ocular disorder comprising implanting a device according to the present disclosure in an eye of a subject. The term "ocular disorder" herein refers to any disease or disorder of the eye or related tissues (i.e. retina, macula, retinal blood vessels, etc.) or any symptom thereof. Non-limiting examples of ocular disorders include macular degeneration (e.g., exudative and non-exudative age-related macular degeneration), bull's eye maculopathy, cataract, central serous retinopathy, chorioretinal scars, chorioretinitis, chorioretinitis from toxoplasma, chorioretinitis from tuberculous, choroid, choroidal (central areolar, choroidal atrophy, choroidal degeneration, choroidal detachment, choroidal haemorrhage, choroidal haemorrhage and rupture, choroidal neovascularization, choroidal sclerosis, choroideremia, choroiditis, cystoid macular edema, detachment of retinal pigment epithelium, diabetic retinopathy, dystrophy, epiretinal membrane, generalized, gyrate atrophy, glaucoma, Harada's disease, hereditary choroidal dystrophy, diabetic macular edema, cystoid macular edema, hereditary retinal dystrophy, hypertensive retinopathy, macula scars of posterior pole (postinflammatory or posttraumatic), macular edema, or peripapillary, pars planitis, papillitis, peripheral retinal degeneration, posterior cyclitis, retinal detachment, retinal haemorrhage, retinal neovascularization, retinal vascular occlusions, retinitis, retinitis, retinitis, retinitis pigmentosa, retinochoroiditis, retinochoroiditis, retinochoroiditis, retinopathy, retinopathy of prematurity, retinoschisis, separation of retinal layers, solar retinopathy, syphilitic chorioretinitis, infectious and non-infectious uveitis, retinal artery occlusion, retinal vein occlusion, retinal and choroidal angiogenesis or neovascularization, retinal and choroidal ischemia, and other ocular events.

In one embodiment, the present disclosure provides an implantable device comprising a substrate capable of capturing a target molecule present in the eye and/or from fluid of the eye (e.g., an intraocular target molecule). Generally, substrates suitable for use in a device consistent with this disclosure have large surface areas and high affinities for an angiogenic compound, such as VEGF, or other proteins associated with ocular disease. In some embodiments, the substrate comprises hydroxyapatite, a ceramic (e.g., a bioceramic), tricalcium phosphate, bioglass, glass, bone, calcium phosphate, metallic alloys, a membrane or a combination thereof. As used herein, the term "hydroxyapatite" refers to a mineral having a formula $Ca_{10}(PO_4)_6(OH)_2$. In some embodiments, the substrate comprises, consists essentially of, or consists of hydroxyapatite. In some embodiments, the substrate comprises, consists essentially of, or consists of a ceramic such as mesoporous hydroxyapatite (MHA). In some embodiments, the substrate does not include a polyethylene glycol-conjugated oligonucleotide. In some embodiments, the substrate comprises, consists essentially of, or consists of polyacrylonitrile, biomedical polymers, polystyrene, polyvinyl chloride, poly(D, L-lactide), polymethyl methacrylate (PMMA), and poly(2-hydroxyethyl methacrylate)PHEMA, acrylic, silicone, dextran, bisacrylamide, alkyl chains, agarose, polyacrylamide, silica, nanoparticles, shape memory polymers, alumina, silicon, graphite, grapheme, gold, DMPC, phospholipid membranes, chitosan, collagen, and/or glycosaminoglycan. In other embodiments, the substrate may be a shape memory polymer, plastic, acrylic, nylon, or a combination of various materials. In some embodiments, the substrate comprises, consists essentially of, or consists of a solid, a porous matrix, a gel, a sheet, a membrane, a colloid, a microparticle, or a nanoparticle. In some embodiments the substrate is durable. In other embodiments, the substrate is dissolvable and/or biodegradable. In some embodiments, the substrate comprises biodegradable pellets that can be injected intravitreally and that subsequently degrade or dissolve. In one embodiment, the device is coated with antibodies specific to a target protein, molecule, or moiety, including those belonging to inflammatory, angiogenic, or infectious etiologies.

In some embodiments, the device is capable of being implanted through an incision. In some embodiments, the device is capable of being implanted by injection. In some embodiments, the device is capable of being implanted in and/or through (e.g., is in contact with) tissue of an eye, for example in or through the pars plana.

Vascular endothelial growth factor (VEGF) is a protein that promotes vasculogenesis and angiogenesis, and is known to mediate retinal neovascularization. Overexpression (among other factors) can therefore lead to ocular disorders such as macular degeneration or age-related macular degeneration. In some embodiments, the target molecule is a protein. In some embodiments, the target molecule is an angiogenic compound, such as VEGF. In some embodiments, the angiogenic compound comprises a human isoform of VEGF, such as one or more of $VEGF_{121}$, $VEGF_{121}b$, $VEGF_{145}$, $VEGF_{165}$, $VEGF_{165}$, $VEGF_{165}b$, $VEGF_{189}$, or $VEGF_{206}$. In some embodiments, the target molecule is adversely associated with retinal physiology, such as PEDF. In other embodiments, the target molecule is selected from: Bone morphogenetic protein-2 (BMP2), Hypoxia-inducible factor-1α (HIF-1α), P2X2, Taurine, Advance glycation end products, Claudin-5, Occludin and JAM-A, microRNAs, RhoJ Pathway, Caveolin-1 (Cav-1), Apelin-13, Exendin-4 and GLP-1, Vascular adhesion protein-1, Angiopoietin-like protein 4 (ANGPTL4), IL-6, IL-8, CXCR3, (CCL2?), MMP-2, 7, and/or 9, TIMP (MMP inhibitors) 1, 2, and/or 3, Cathepsins D, Cystatins, High Temperature required factor A (HtrA) 4, HtrA1 SNP rs11200638, Urokinase-type plasminogen activator, Tissue-type plasminogen activator, IL-6, IL-8, and/or IL-17, IL-2 and TNFa, Pigment epithelium derived growth factor, Placental growth factor, Fibroblast growth factor, Heat shock proteins (HSP27), Human factor H-related protein 2—(CFHR2), IGF-1 and IGFBP-2, INF-gamma and TNFa, Norrin, Neural cell adhesion molecule (N-CAM), Erythropoietin (EPO) and IGF-1, Angiopoietin-1, IL-1B, Nox and RAAS, Apelin/APJ system, 15-lipoxygenase-1 (15-LOX-1), Prolactine and vasoinhibins, TNF, MCP-1, MCP-2, any molecule involved in the complement cascade, oxygen free radicals, apolipoproteins, lipofuscin, and/or inflammatory proteins or those of an infectious etiology.

In some embodiments, the substrate has a relatively high affinity for a target molecule. In some embodiments, the substrate has a relatively high affinity for an angiogenic compound. In some embodiments, the substrate has a higher affinity for an angiogenic compound (e.g., VEGF) than for a VEGF antagonist such as ranibizumab, bevacizumab or pegaptanib.

In some embodiments, the adsorptive property of the device is capable of being regenerated in situ. As used herein, the phrase "capable of being regenerated in situ" indicates that the device is configured such that at least some of the target molecule captured in (or on) the device can be released or expelled from the device in a modified form without the need to remove the device from the subject, so that an additional amount of the target molecule can be captured by the device without implanting a second device in the subject. For example, in one embodiment the device can be regenerated by absorbing energy (e.g., heat) from a source external to the subject. In such an embodiment, the absorbed heat modifies the target molecule (e.g., denatures a protein) such that in its modified form it is characterized by a modified biological activity (e.g., a reduced level of its original biological activity, a different biological activity, or no biological activity). As one example, in one embodiment, the device is capable of adsorbing and/or absorbing VEGF and, after exposure to a thermal source (e.g., a thermal laser such as an argon laser, a diode, a femtosecond laser, a neodymium-doped yttrium aluminum garnet (Nd:Yag) laser, a photodynamic laser, a photodisruptive laser, or a combination thereof), is capable of releasing denatured VEGF. In another embodiment, the device is regenerated by applying cryotherapy to the device. Without wishing to be bound by theory, in such an embodiment it is believed that the decrease or increase in temperature of the adherent proteins causes denaturation and inactivation of biological activity. Alternatively, electrical current or electromagnetic energy may be passed through the device to cause protein denaturation. Further, changing the local pH, desiccation, radiation, or doping with elements may all be used to interfere or degrade the biological function of the target protein. Photodynamic therapy, or other light-sensitive materials, may be used to inactivate the adherent proteins. Additionally, the process of laser induced surface plasmon resonance such as with quantum dots may be used to generate a local thermal reaction. Accordingly, in some embodiments, the device has a higher affinity for the target molecule compared to its corresponding modified target molecule (e.g., its thermally denatured target molecule). In some embodiments, the modified target molecule comprises one or more degradation products of the target molecule. Further, the substrate may be treated with fluorophores or other chemical moieties such that the amount of protein adsorbed to the surface is visible by color change, perceptible by indirect ophthalmoscopy, direct visualization, or using confocal scanning laser technology, filters, or other means. The implant may be translucent or clear, allowing the practitioner to laser all surfaces by means of adjusting the laser's focal point. Further, solid implants may be capable of rotating along the major axis, allowing the practitioner to visualize and apply laser energy to the surface in its entirety.

In some embodiments, the present disclosure provides an implantable device comprising a substrate comprising one or more of hydroxyapatite and a ceramic, and a captured angiogenic compound. In some embodiments, the device is capable of releasing the captured angiogenic compound (and/or modified angiogenic compounds, degradation products of the angiogenic compound, etc.) after denaturation of at least a portion of the captured angiogenic compound, for example by exposure to a laser. In some embodiments, the device is capable of capturing an additional amount of the angiogenic compound after exposure to the laser. In some embodiments, the angiogenic compound comprises VEGF (e.g., a human isoform of VEGF) from vitreous fluid of a subject.

In some embodiments, such as the embodiment shown in FIG. 1, at least a portion of the implantable device 100 has a size and shape that imparts a relatively high surface area to the device. For example, in one embodiment device 100 comprises an anchoring portion 110 and an immersed or immersible portion 120, wherein the anchoring portion 110 is configured to be in contact with and secured at one or more tissues of the eye, and wherein immersed or immersible portion 120 is configured to be in contact with vitreous fluid 18. In some embodiments, immersed or immersible portion 120 defines a size and shape different from that of an anchoring portion 110 of device 100. Immersed or immersible portion 120 of the device 100 may have a polygon shape, or a shape of a cylinder, sphere, partial sphere, cone, truncated cone, or a combination thereof. The device may also be composed of multiple hollow tubes, similar to dialysis tubing, which can be bundled together.

In some embodiments, the device 100 has an anchor portion 110 with which the device can be attached to a portion of the eye tissue, for example by suture.

In some embodiments, the device 100 has an indicator portion 130 which may be used, for example, to provide a practitioner with information about the type of material(s) used in device 100. In other embodiments, indicator portion 130 may provide the practitioner a target zone or information about where a regenerating laser may be focused.

Figure 2:
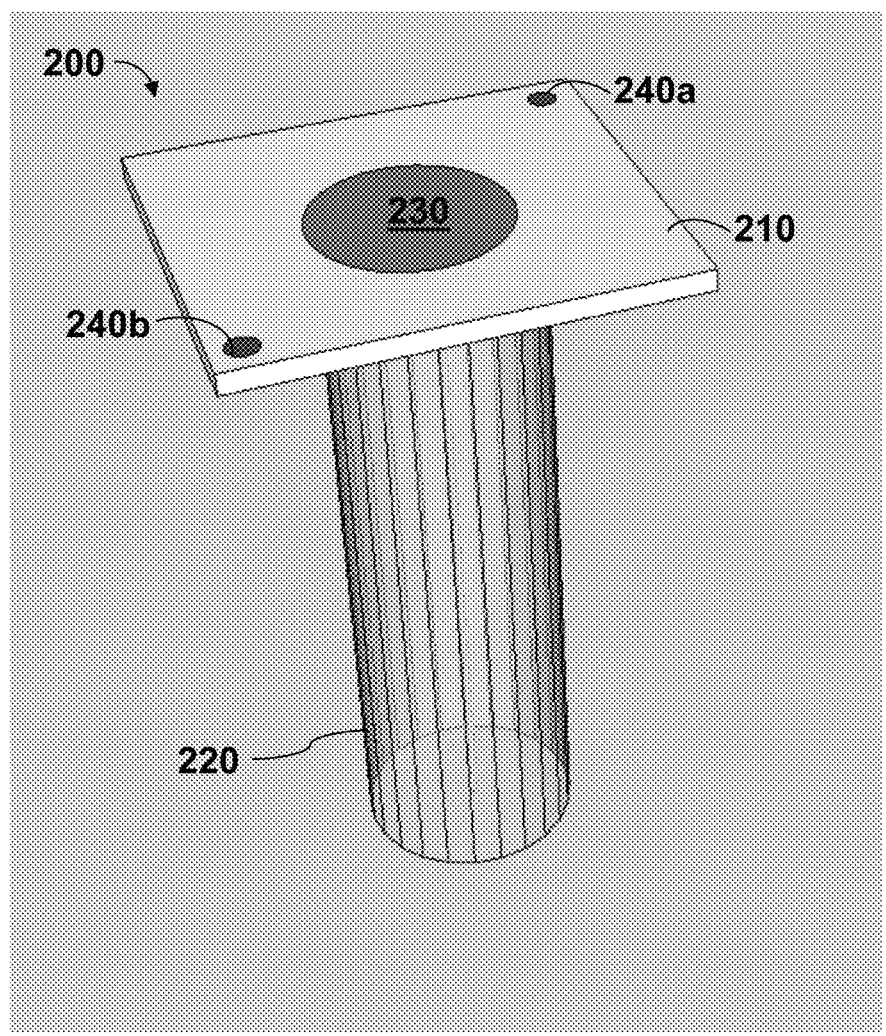
FIG. 2 depicts a portion of one embodiment of a device of the present disclosure having a generally cylindrical cross section.

In other embodiments, for example as shown in FIG. 2, an implantable ocular device 200 comprises an anchoring portion 210 and an immersed or immersible portion 220. In some embodiments, device 200 includes one or more anchoring features (240a, 240b) which allow a practitioner to secure device 200 to a tissue of the eye. For example, anchoring feature(s) 240a-b may comprise holes through which a suture can be passed. In some embodiments, the substrate may be incorporated into other implants which are commonly placed in the eye such as glaucoma drainage devices, aqueous shunting devices, and intraocular lenses.

In some embodiments, immersed or immersible portion 220 of device 200, may have a generally cylindrical, tapered cylinder, or conical cross section. Further, it may be spherical, tubular, or in a sheet-like configuration. In some embodiments, device 200 has an indicator portion 230 which may be used, for example, to provide a practitioner with information about the type of material(s) used in device 200. In other embodiments, indicator portion 230 may provide the practitioner a target zone or information about where a regenerating laser may be focused. In some embodiments, indicator portion 230 is applied to or formed as part of anchoring portion 210. In some embodiments, indicator portion 230 is configured to allow a needle to pass therethrough, for example to allow removal, replacement, or exchange of materials inside immersed or immersible portion 220 without removing device 200 from the eye. In some embodiments, indicator portion 230 comprises a self-sealing material, for example to prevent fluid from passing therethrough after penetration by a needle.

In some embodiments at least a portion of the implantable device (e.g., immersed or immersible portion 120, 220) has a porous or microporous surface. In some embodiments, the surface of at least a portion of device has an average pore diameter of less than 1 mm, for example about 1 mm, about 0.95 mm, about 0.9 mm, about 0.85 mm, about 0.8 mm, about 0.75 mm, about 0.7 mm, about 0.65 mm, about 0.6 mm, about 0.55 about 0.5 mm, about 0.45 mm, about 0.4 mm, about 0.35 mm, about 0.3 mm, about 0.25 mm, about 0.2 mm, about 0.15 mm, about 0.1 mm, about 0.05 mm, or less than about 0.05 mm.

In some embodiments, the implantable device is further capable of delivering a drug to the subject. In some embodiments, the drug is an anti-VEGF compound such as ranibizumab, bevacizumab or pegaptanib, or a steroid. The drug may be loaded into the substrate by forced pressure or vacuum techniques, filling the porous cavities of the device with the intended therapeutic agent, whether solid, powder, liquid, or gas.

In one embodiment, the present disclosure provides a method of treating an ocular disorder in a subject, the method comprising implanting into an eye of the subject, and in contact with fluid of the eye, a device as disclosed herein; and thereafter capturing the target molecule from the fluid. In one embodiment, the eye has previously undergone vitrectomy or other ocular surgery.

One embodiment of a method of the present disclosure is depicted in FIG. 1. A device of the present disclosure 100 is implanted in the eye 10 of the subject. In some embodiments, the device 100 is implanted through (e.g., is in contact with) one or more of: the sclera 16, the choroid 14, and/or the retina 12. In some embodiments, the device 100 implanted through (e.g., is in contact with) the pars plana portion of the choroid 14.

In some embodiments, the method further comprises, after capturing the target molecule from fluid of the eye, regenerating the adsorptive properties of the device in situ. In some embodiments, the step of regenerating the device in situ comprises exposing the device to an energy source, such as a laser, for example from a laser indirect opthalmoscope.

In some embodiments, the method further comprises, after regenerating the device in situ, capturing an additional amount of the target molecule from fluid of the eye.

In some embodiments, the implanted device is left in place for a period of time sufficient to reduce or alleviate one or more symptoms of the ocular disorder, for example about one month, about 2 months, about 3 months, about 4 months, about 5 months, about 6 months, about 7 months, about 8 months, about 9 months, about 10 months, about 11 months, about 12 months, or more than 12 months. In some embodiments, the device is regenerated at least once, at least twice, at least 3 times, at least 4 times, at least 5 times, at least 6 times, at least 7 times, at least 8 times, at least 9 times, at least 10 at least 11 times, at least 12 times, or more than 12 times before removal from the subject. In an alternative embodiment, the device is removed after a period of time sufficient for it to become saturated with the target molecule, for example after about 1 about 2 weeks, about 3 weeks, about 4 weeks, about 5 weeks, about 6 weeks, about 7 weeks, about 8 weeks, about 9 weeks, about 10 weeks, about 11 weeks, about 12 about 4 months, about 5 months, about 6 months, about 7 months, about 8 about 9 months, about 10 months, about 11 months, about 12 months.

In some embodiments, a method of treating an ocular disorder in a subject on intraocular injection therapy comprises, consists essentially of, or consists of optionally identifying the subject as being on intraocular injection therapy; implanting into an eye of the subject, and in contact with fluid of the eye, a device comprising a substrate capable of capturing a target molecule present in fluid of the eye; capturing the target molecule from the fluid; and optionally after capturing the target molecule from the fluid, regenerating the device in situ. In some embodiments, the intraocular injection therapy comprises administration of ranibizumab, bevacizumab and/or pegaptanib. In some embodiments, the target molecule is an angiogenic compound, optionally VEGF. In some embodiments, the optional step of regenerating the device in situ comprises contacting the device with a thermal laser to denature and/or decompose at least a portion of the captured target molecule.

In some embodiments, a method of the present disclosure comprises replacing existing intraocular injection therapeutic regimen with a second treatment regimen comprising, consisting essentially of, or consisting of implanting into an eye of the subject, and in contact with fluid of the eye, a device comprising a substrate capable of capturing a target molecule present in fluid of the eye; capturing the target molecule from the fluid; and optionally after capturing the target molecule from the fluid, regenerating the device in situ. In some embodiments, the existing intraocular injection therapy is discontinued before, concomitantly with, or after implanting the device into the eye of the subject. In some embodiments, the target molecule is an angiogenic compound, optionally VEGF. In some embodiments, the optional step of regenerating the device in situ comprises contacting the device with a thermal laser to denature and/or decompose at least a portion of the captured target molecule.

EXAMPLES

Example 1: Acute Model

Twenty white cross rabbits are divided into three groups: control, active implant (bioceramic), and inactive implant (standard plastic). Baseline photographs, electroretinograms, and intravitreal VEGF levels are performed on all subjects. The active and inactive implant groups undergo surgery and two weeks later all three groups receive in the right eye a standardized dose of VEGF in a polymer pellet which has a sustained release profile sufficient to induce vasoproliferation in a reliable and repeatable manner. Repeat examinations, fundus photography, fluorescein angiography, and intravitreal VEGF sampling are performed at 24 hrs, 48 hrs, 4 days, 7 days, 14 days, 21 days, and 28 post-surgery. Prior to harvesting the eyes for histological examination, final electroretinograms are performed. Subsequent grading of observed neovascularization is performed by a masked observer using the system described by Ozaki et al., "Intravitreal sustained release of VEGF causes retinal neovascularization in rabbits and breakdown of the blood-retinal barrier in rabbits and primates," *Exp. Eye Res.*, vol. 64(4), pages 505-17 (1997).

Example 2: Chronic Model

A subset of subjects from Example 1 are observed for an additional 9 months in order to determine long-term stability and biocompatibility of the implanted device. Exams, fundus photography, angiography, electroretinography and VEGF sampling are performed each month.

Example 3: Regeneration of Implantable Devices by Thermal Laser

Bioceramic discs composed of porous hydroxyapatite were soaked overnight in 50 μL of deionized water containing 50 ng of VEGF, each in a separate well of a 96-well plate. The discs soaked for 24 hours with periodic gentle agitation, after which the excess solution was removed. The amount of VEGF in this solution was determined using a human VEGF ELISA kit. The estimated amount of VEGF loaded into the implant was determined by subtracting the amount in the solution from the loading amount. The hydroxyapatite discs adsorbed an average of 14 ng of VEGF, compared to less than 1 ng for a control group consisting of plastic beads ($p<0.05$).

Next, half of the hydroxyapatite discs were exposed to argon laser (240 mW power, 0.2 ms duration, 100 spots over 2 minutes), sufficient to induce a rise in the surface temperature of the discs of 8° C., as measured by an infrared thermometer. The other half of the pellets were exposed to light for 2 minutes, without exposure to laser and without surface temperature change. All the pellets were then placed in separate wells of another 96-well plate and allowed to soak 48 hours in DI water with gentle agitation. The amount of VEGF released from each pellet was then measured again using the VEGF ELISA kit. The discs exposed to light released about 30% of the initial loading dose of VEGF, compared to about 5% in the lasered group (p<0.05). These data demonstrate that the bioceramic material can sequester VEGF, which can be further inactivated by thermal laser.

Example 4: Adsorption of Complement Factor D by PAN Fibers

An experiment was conducted to assess adsorption of complement Factor D by PAN fibers as compared to polypropylene capillaries according to the below protocol.

Hydrate and Equilibrate PAN and polypropylene fibers
  Cut PAN fibers into small fragments <4 mm in length[1]
  Measure 3 samples each of 50 mg PAN and polypropylene fibers in separate eppendorf tubes [45 mg max amount used by Pascual and Schifferli[1] however they had a slightly lower amount of Complement Factor D in their samples]
  Add 675 ul Elisa wash/dilution buffer (W/d b) into each tube [since Elisa is going to be used to analyze the samples]
  Mix well by tapping
  Incubate at 37 degree C. for 1 hour[1] [alternatively could incubate at room temperature for 12 hours]
  Wash twice with 675 ul W/d b at room temp
  Suspend in 675 ul W/d d at room temp
Prepare samples:
Negative Control (NC): 3 samples
  Tube 1: total volume 675 ml [20 ng/ml CF-D concentration, maximal concentration detected by Elisa kit]
  672 ul W/d b
  13.2 ng Complement Factor D (CF-D) (3 ul of 4.4 ng/ul CF-D standard) [3 ul=12.5 ng used by Pascual and Schifferli[1]]
  Mix well by tapping
  Tube 2: total volume 675 ml
  672 ul W/d b
  13.2 ng CF-D (3 ul of 4.4 ng/ul CF-D standard)
  Mix well by tapping
  Tube 3: total volume 675 ml
  672 ul W/d b
  13.2 ng CF-D (3 ul of 4.4 ng/ul CF-D standard)
  Mix well by tapping
Experiment (E): 3 samples
  Tube 1: total volume 675 ml [20 ng/ml CF-D concentration, maximal concentration detected by Elisa kit]
  672 ul W/d b (room ten solution)
  13.2 ng CF-D (3 ul of 4.4 ng/ul CF-D standard) [3 ul=12.5 ng used by Pascual and Schifferli[1]]
  Mix well by tapping
  Add 50 mg hydrated and equilibrated PAN membranes
  Mix well by tapping
  Tube 2: total volume 675 ml
  672 ul W/d b (room temp solution)
  13.2 ng CF-D (3 ul of 4.4 ng/ul CF-D standard)
  Mix well by tapping
  Add 50 mg hydrated and equilibrated polypropylene membranes
  Mix well by tapping
  Tube 3: total volume 675 ml
  672 ul W/d b (room temp solution)
  13.2 ng CF-D (3 ul of 4.4 ng/ul CF-D standard)
  Mix well by tapping
  Add 50 mg hydrated and equilibrated polypropylene membranes
  Mix well by tapping
Sham (S): 3 samples
  Tube 1: total volume 675 ml [20 ng/ml CF-D concentration, maximal concentration defected by Elisa kit]
  672 ul W/d b (room temp solution)
  13.2 ng CF-D (3 ul of 4.4 ng/ul CF-D standard) [3 ul=12.5 ng used by Pascual and Schifferli[1]]
  Mix well by tapping
  Add 50 mg hydrated and equilibrated polypropylene membranes
  Mix well by tapping
  Tube 2: total volume 675 ml
  672 ul W/d b (room temp solution)
  13.2 ng CF-D (3 ul of 4.4 ng/ul CF-D standard)
  Mix well by tapping
  Add 50 mg hydrated and equilibrated polypropylene membranes
  Mix well by tapping
  Tube 3: total volume 675 ml
  672 ul W/d b (room temp solution)
  13.2 ng CF-D (3 ul of 4.4 ng/ul CF-D standard)
  Mix well by tapping
  Add 50 mg hydrated and equilibrated polypropylene membranes
  Mix well by tapping
Incubate samples for 1 hour at 37 degree C. [alternatively could incubate at room temperature for 12 hours; then it would not be needed to bring samples to room temperature for analysis after incubation]
Prepare serial dilution for calibration curve according to serial dilution protocol per Hycult Biotech CFD Elisa Kit manual (p. 7) with the following concentrations:
  Tube 1: 20 ng/ml
  Tube 2: 13.3 ng/ml
  Tube 3: 8.9 ng/ml
  Tube 4: 5.9 ng/ml
  Tube 5: 4.0 ng/ml
  Tube 6: 2.6 ng/ml
  Tube 7: 1.8 ng/ml
  Tube 8: 0 ng/ml (blank; W/d b only)
Take samples out of 37 degree incubator, mix samples well by tapping, and transfer 375 ul out of each sample tube into a new eppendorf tube at room temperature to be used for Elisa analysis
Keep to-be-analyzed samples at room temperature for 1 hour, since room temperature is required for Elsa analysis
Perform ELISA on the prepared samples (3×100 ug wells per sample) following the protocol per Hycult Biotech CFD Elisa Kit manual (p. 9)
Well Lay-Out:

| T1 | T1 | NC1 | NC1 | NC1 | NC2 |
|----|----|-----|-----|-----|-----|
| T2 | T2 | NC2 | NC2 | NC3 | NC3 |
| T3 | T3 | NC3 | E1 | E1 | E1 |
| T4 | T4 | E2 | E2 | E2 | E3 |
| T5 | T5 | E3 | E3 | S1 | S1 |
| T6 | T6 | S1 | S2 | S2 | S2 |
| T7 | T7 | S3 | S3 | S3 | empty |
| T8 | T8 | empty | empty | empty | empty |

- Measure absorbance at 450 nm

Reference:
1. Pascual, M. and J. A. Schifferli (1993). "Adsorption of complement factor D by polyacrylonitrile dialysis membranes." *Kidney Int* 43(4): 903-911.

Figure 3:
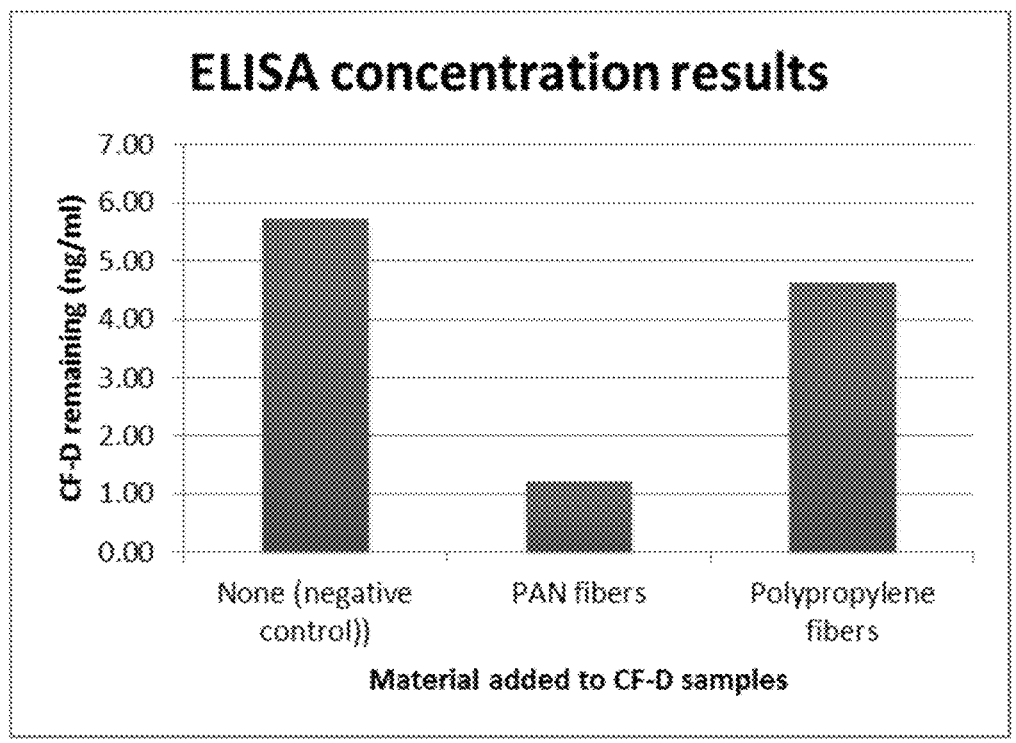
FIG. 3 shows ELISA concentration results when complement Factor D (CFD) was incubated in vials containing polyacrylonitrile (PAN) dialysis fibers, a control containing polypropylene fibers, and a negative control. The solution remaining was then examined using spectrophotometry. The results indicate that PAN is taken up in very high amounts by the PAN membranes compared to the controls.
Figure 4:
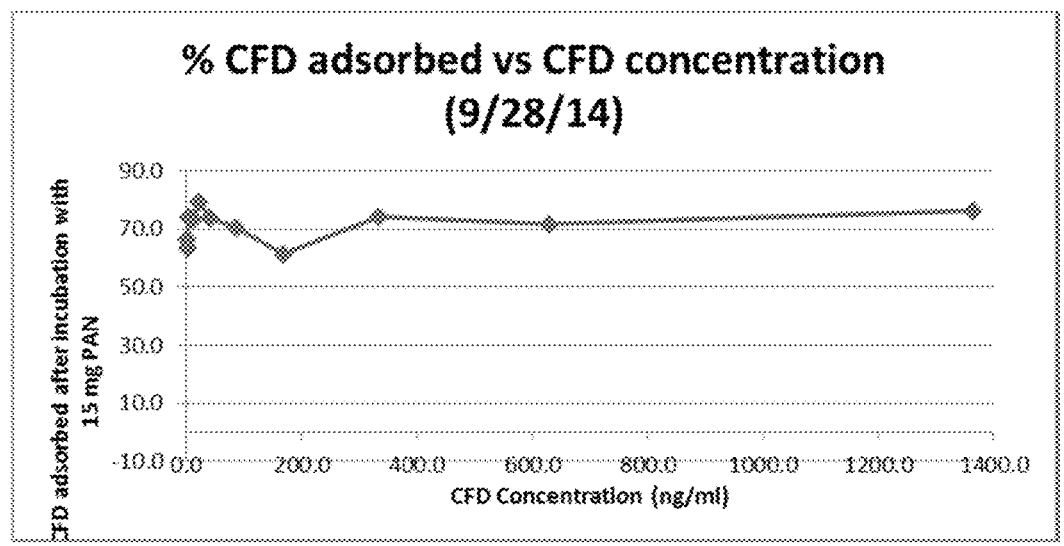
FIG. 4. demonstrates that when CFD is incubated with PAN membranes, the protein is taken up by the membrane well, and even at very high concentrations does not show saturation, indicating that the membrane can adsorb very high levels of the protein.

Results are shown in FIGS. 3 and 4. Overall, these experiments demonstrate that a type of membrane (polyacrylonitrile) will adsorb high amounts of a protein called Complement Factor D (CFD), which is thought to be a major therapeutic target in dry macular degeneration.

Example 5: In Vitro VEGF Adsorption

An in vitro adsorption experiment was conducted according to the following protocol:

Three groups were tested: hydroxyapatite implant, acrylic bead, and control. A total of nine wells were used, three per group, and the experiment run three times. Each well contained a standard concentration of VEGF 400 pg/mL. The implants and beads were pieced in the respective wells, and all wells kept at 4 degrees Celsius for 24 hours. The hydroxyapatite implants and the acrylic beads were then removed from solution, washed with saline, and the amount of VEGF removed by washing measured and added to the total VEGF measured in solution. There was a statistically significant difference between the hydroxyapatite group and the acrylic bead and control groups, but not between the acrylic bead and control group ($p<0.05$).

For the hydroxyapatite group, a mean of 64 pg/mL of VEGF remained in solution, compared to 359 pg/mL and 369 pg/mL for the acrylic bead and control groups respectively. The amount of VEGF adsorbed is obtained by subtracting the VEGF remaining in solution from the total initial concentration. The HA implant adsorbed on average 336 pg/ml, compared to 41 pg/mL for the acrylic bead group and 31 pg/mL for the control group.

Figure 5:
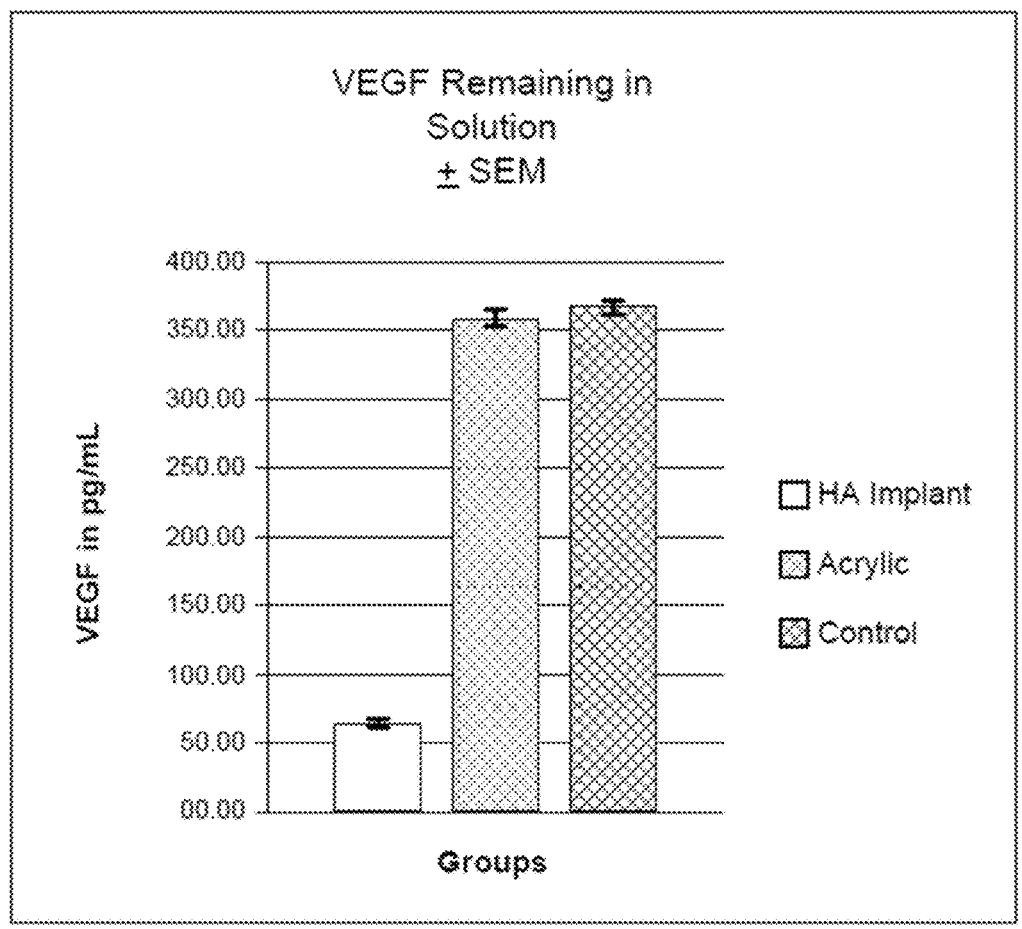
FIG. 5 shows results of an in vitro VEGF adsorption assays and in particular that VEGF levels remaining in solution were significantly lower in the HA implant group, indicating that VEGF is strongly adsorbed by the hydroxyapatite implant.

Results are shown in FIG. 5 and demonstrate that VEGF levels remaining in solution were significantly lower in the HA implant group, indicating that VEGF is adsorbed by the hydroxyapatite implant.

From the foregoing, it will be appreciated that specific embodiments of the invention have been described herein for purposes of illustration, but that various modifications may be made without deviating from the scope of the invention.

I claim:

1. A method of treating macular degeneration in a subject, the method comprising the steps of:
    implanting into an eye of the subject, and in contact with a fluid of the eye, a device comprising polyacrylonitrile fibers;
    the polyacrylonitrile fibers having a high affinity for and capturing complement factor D from the fluid;
    leaving the device in the eye for a period of time to reduce or alleviate one or more symptoms of macular degeneration; and
    regenerating the device in situ by exposing the device to a thermal laser sufficient to denature and release a captured amount of the complement factor D.

2. The method of claim 1, wherein the polyacrylonitrile fibers substrate comprise a hollow tube.

3. The method of claim 2, wherein the polyacrylonitrile fibers comprise a plurality of hollow tubes bundled together.

4. The method of claim 1, wherein the polyacrylonitrile fibers are a solid, a porous matrix, a gel, a sheet, a membrane, a colloid, a microparticle, a nanoparticle, or does not include a polyethylene glycol-conjugated oligonucleotide.

5. The method of claim 1, wherein the polyacrylonitrile fibers are incorporated into one of a glaucoma drainage device, an aqueous shunting device, an intraocular lens, and a drug delivery device.

6. The method of claim 1, further comprising the steps of anchoring the device to a tissue of the eye.

7. The method of claim 1, further comprising the steps of securing the polyacrylonitrile fibers in one of an anterior chamber and a vitreous cavity of the eye.

8. The method of claim 1, wherein the period of time is at least 6 months.

9. The method of claim 1, wherein the device has a higher affinity for the complement factor D compared to a corresponding denatured complement factor D.

10. The method of claim 1, further comprising the step of regenerating the device in situ at least twice.

11. The method of claim 1, further comprising the step of regenerating the device in situ at least 4 times.

12. The method of claim 1, wherein the device is coated with an antibody specific to the complement factor D.

13. The method of claim 1, wherein the polyacrylonitrile fibers are treated with a chemical moiety such that the amount of the complement factor D adsorbed to the surface is visible by color change.

14. A method of treating retinal neovascularization in a subject, the method comprising the steps of:
    implanting into an eye of the subject, and in contact with a fluid of the eye, a device comprising hydroxyapatite;
    the hydroxyapatite having a high affinity for and capturing vascular endothelial growth factor from the fluid;
    leaving the device in the eye for a period of time to reduce or alleviate one or more symptoms of retinal neovascularization; and
    regenerating the device in situ by exposing the device to a thermal laser sufficient to denature and release a captured amount of the vascular endothelial growth factor.

15. The method of claim 14, wherein the hydroxyapatite is a solid, a porous matrix, a gel, a sheet, a membrane, a colloid, a microparticle, a nanoparticle, or does not include a polyethylene glycol-conjugated oligonucleotide.

16. The method of claim 14, wherein the hydroxyapatite is incorporated into one of a glaucoma drainage device, an aqueous shunting device, an intraocular lens, and a drug delivery device.

17. The method of claim 14, wherein the period of time is at least 6 months.

18. The method of claim 14, wherein the device has a higher affinity for the vascular endothelial growth factor compared to a corresponding denatured vascular endothelial growth factor.

19. The method of claim 14, further comprising the step of regenerating the device in situ at least twice.

20. The method of claim 14, wherein the hydroxyapatite is treated with a chemical moiety such that the amount of the vascular endothelial growth factor adsorbed to the surface is visible by color change.

* * * * *